(12) United States Patent
Jilka et al.

(10) Patent No.: US 6,977,325 B2
(45) Date of Patent: Dec. 20, 2005

(54) PLANT PROMOTER SEQUENCES AND METHODS OF USE FOR SAME

(76) Inventors: Joseph M. Jilka, 2308 Ferguson, College Station, TX (US) 77845; Elizabeth E. Hood, 8605 Amber Hill Ct., College Station, TX (US) 77845; John A. Howard, 5819 Stallion Ridge Rd., College Station, TX (US) 77845

(*) Notice: Subject to any disclaimer, the term of this patent is extended or adjusted under 35 U.S.C. 154(b) by 7 days.

(21) Appl. No.: 10/086,062

(22) Filed: Feb. 28, 2002

(65) Prior Publication Data

US 2003/0066108 A1 Apr. 3, 2003

Related U.S. Application Data

(63) Continuation of application No. 09/590,558, filed on Jun. 9, 2000, now abandoned.

(51) Int. Cl.[7] .................. C12N 15/00; C12N 15/82; C12N 15/87; C07H 21/04; C12P 21/06
(52) U.S. Cl. ............... 800/278; 435/69.1; 435/320.1; 435/419; 435/440; 435/468; 536/23.6; 536/24.1
(58) Field of Search ......................... 435/320.1, 419, 435/410, 69.1, 440, 468, 325; 536/23.6, 24.1, 23.1; 800/278

(56) References Cited

U.S. PATENT DOCUMENTS

| 5,510,474 A | | 4/1996 | Quail et al. ............ 536/24.1 |
| 6,054,574 A | * | 4/2000 | Quail et al. ............ 536/24.1 |

FOREIGN PATENT DOCUMENTS

| EP | 0 342 926 A2 | | 11/1989 |
| EP | 0 342 926 A | | 11/1989 |
| EP | 0342926 | * | 11/1989 |
| EP | 99307158.8 | | 9/1999 |
| WO | WO00/15810 | * | 3/2000 |
| WO | WO 01/18220 | | 3/2001 |

OTHER PUBLICATIONS

Peter et al. The Plant Cell, vol. 5, pp. 877–886, Aug. 1993.*
Almoguera Concepcion et al., "Dual regulation of a heat shock promoter during embryogenesis: Stage–dependent role of heart shock elements", *Plant Journal*, vol. 13(4) 437–446 (Feb. 1998).
Praendl Ralf et al., "Heat shock elements are involved in heat shock promoter activation during tobacco seed maturation", *Plant Molecular Biology*, vol. 31(1) 157–162 (1996).
Geneschik, P., et al., "Structure and promoter activity of a stress and developmentally regulated polyublquitin–encoding gene of *Nicotiana tabacum*", *Gene*, 148:195–202 (1994).
Kawalleck, P., et al., "Polyubiquitin gene expression and structural properties of the *ubiA*–2 gene in *Petroselinum crispum*", *Plant Molecular Biology*, 21:673–684 (1993).
Liu, L., et al., "Characterization, chromosomal mapping, and expression of different polyubiquitin genes in tissues from control and heat–shocked maize seedlings", *Biochem. Cell Biol.*, 73:19–30 (1995). Printed in Canada.
Lopes, Mauricio A. et al. "Synthesis of an Unusual α–Zein Protein is Correlated With the Phenotypic Effects of the *Foury2* Mutation in Maize", *Mol. Gen. Genet*, 1994, vol. 245, pp. 537–547.
Coleman, Craig E. et al., "Expression of a Mutant α–Zein Creates the *Foury2* Phenotype in Transgenic Maize", *National Academy of Sciences*, 1997, vol. 94, pp. 7094–7097.

* cited by examiner

*Primary Examiner*—Janet L. Epps-Ford
(74) *Attorney, Agent, or Firm*—McKee, Voorhees & Sease, P.L.C.

(57) ABSTRACT

The invention discloses novel promoter sequences capable of expressing genes in plant cells. The promoters include engineered versions of the maize ubiquitin promoter to increase expression levels beyond those observed with the native ubiquitin promoter and alter the tissue preference. Expression constructs, vectors, transgenic plants and methods are also disclosed.

2 Claims, 6 Drawing Sheets

SEQUENCE LISTING

<160> NUMBER OF SEQ ID NOS: 14

<210> SEQ ID NO 1
<211> LENGTH: 25
<212> TYPE: DNA
<213> ORGANISM: Agrobacterium tumefaciens

<400> SEQUENCE: 1
ctggacccct ctcgagagtt ccgct                                           25

<210> SEQ ID NO 2
<211> LENGTH: 15
<212> TYPE: DNA
<213> ORGANISM: Agrobacterium tumefaciens

<400> SEQUENCE: 2
ctggacccct ctcga                                                      15

<210> SEQ ID NO 3
<211> LENGTH: 15
<212> TYPE: DNA
<213> ORGANISM: Agrobacterium tumefaciens

<400> SEQUENCE: 3
ctcgagagtt ccgct                                                      15

<210> SEQ ID NO 4
<211> LENGTH: 30
<212> TYPE: DNA
<213> ORGANISM: Agrobacterium tumefaciens

<400> SEQUENCE: 4
ctggacccct ctcgactcga gagttccgct                                      30

<210> SEQ ID NO 5
<211> LENGTH: 22
<212> TYPE: DNA
<213> ORGANISM: Agrobacterium tumefaciens

<400> SEQUENCE: 5
gacacgtaga atgagtcatc ac                                              22

<210> SEQ ID NO 6
<211> LENGTH: 13
<212> TYPE: DNA
<213> ORGANISM: Arabidopsis thaliana

<400> SEQUENCE: 6
atggcggctc tta                                                        13

<210> SEQ ID NO 7
<211> LENGTH: 13
<212> TYPE: DNA
<213> ORGANISM: Arabidopsis thaliana

<400> SEQUENCE: 7
cttccacgtg gca                                                        13

<210> SEQ ID NO 8
<211> LENGTH: 26
<212> TYPE: DNA
<213> ORGANISM: Hordeum vulgare

```
-continued

<400> SEQUENCE: 8
acatgtaaag tgaataaggt gagtca                                        26

<210> SEQ ID NO 9
<211> LENGTH: 22
<212> TYPE: DNA
<213> ORGANISM: Hordeum vulgare

<400> SEQUENCE: 9
ggccgataac aaactccggc cg                                            22

<210> SEQ ID NO 10
<211> LENGTH: 15
<212> TYPE: DNA
<213> ORGANISM: Oryza sativa

<400> SEQUENCE: 10
ccagtgtgcc cctgg                                                    15

<210> SEQ ID NO 11
<211> LENGTH: 10
<212> TYPE: DNA
<213> ORGANISM: Pisum sativum

<400> SEQUENCE: 11
gatttacact                                                          10

<210> SEQ ID NO 12
<211> LENGTH: 16
<212> TYPE: DNA
<213> ORGANISM: Triticum aestivum

<400> SEQUENCE: 12
taaggtgagt catata                                                   16

<210> SEQ ID NO 13
<211> LENGTH: 10
<212> TYPE: DNA
<213> ORGANISM: Zea mays

<400> SEQUENCE: 13
atactttttc                                                          10

<210> SEQ ID NO 14
<211> LENGTH: 18
<212> TYPE: DNA
<213> ORGANISM: Zea mays

<400> SEQUENCE: 14
tgtcattcca cgtagatg                                                 18
```

PLANT PROMOTER SEQUENCES AND METHODS OF USE FOR SAME

This application is a continuation of U.S. application Ser. No. 09/590,558, filed Jun. 9, 2000, now abandoned.

FIELD OF THE INVENTION

This invention relates generally to the field of plant molecular biology and in particular to engineered promoter sequences and their combined arrangement within a promoter region such that expression of an expression construct is enhanced in a plant cell.

BACKGROUND OF THE INVENTION

Gene expression encompasses a number of steps originating from the DNA template, ultimately to the final protein or protein product. Control and regulation of gene expression can occur through numerous mechanisms. The initiation of transcription of a gene is generally thought of as the predominant control of gene expression. Transcriptional controls (or promoters) are generally short sequences embedded in the 5'-flanking or upstream region of a transcribed gene. There are promoter sequences which affect gene expression in response to environmental stimuli, nutrient availability, or adverse conditions including heat shock, anaerobiosis or the presence of heavy metals. There are also DNA sequences which control gene expression during development, or in a tissue, or in an organ specific fashion, and, of course there are constitutive promoters.

Promoters contain the signals for RNA polymerase to begin transcription so that protein synthesis can proceed. DNA binding, nuclear, localized proteins interact specifically with these cognate promoter DNA sequences to promote the formation of the transcriptional complex and eventually initiate the gene expression process. The entire region containing all the ancillary elements affecting regulation or absolute levels of transcription may be comprised of less than 100 base pairs or as much as 1 kilobase pairs.

One of the most common sequence motifs present in the promoters of genes is the "TATA" element which resides upstream of the start of transcription. Promoters are also typically comprised of components which include a TATA box consensus sequence at about 35 base pairs 5' relative to the transcription start site or cap site which is defined as +1. The TATA motif is the site where the TATA-binding-protein (TBP) as part of a complex of several polypeptides (TFIID complex) binds and productively interacts (directly or indirectly) with factors bound to other sequence elements of the promoter. This TFIID complex in turn recruits the RNA polymerase II complex to be positioned for the start of transcription generally 25 to 30 base pairs downstream of the TATA element and promotes elongation thus producing RNA molecules.

In most instances sequence elements other than the TATA motif are required for accurate transcription. Such elements are often located upstream of the TATA motif and a subset may have homology to the consensus sequence CCAAT.

Promoters are usually positioned 5' or upstream relative to the start of the coding region of the corresponding gene, and the entire region containing all the ancillary elements affecting regulation or absolute levels of transcription may be comprised of less than 100 base pairs or as much as 1 kilobase pair.

A number of promoters which are active in plant cells have been described in the literature. These include nopaline synthase (NOS) and octopine synthase (OCS) promoters (which are carried on tumor inducing plasmids of *Agrobacterium tumefaciens*) The cauliflower mosaic virus (CaMV) 19S and 35S promoters, the light-inducible promoter from the small subunit of ribulose bisphosphate carboxylase (ssRUBICSO, a very abundant plant polypeptide), the alcohol dehydrogenase (AdhI and AdhII) promoters from maize, and the sucrose synthase promoter. All of these promoters have been used to create various types of DNA constructs which have been expressed in plants. (See for example PCT publication WO84/02913 Rogers, et al). Perhaps the most commonly used promoter is the 35S promoter of Cauliflower Mosaic Virus. The (CaMV) 35S promoter is a dicot virus promoter, however, it directs expression of genes introduced into protoplasts of both dicots and monocots. The 35S promoter is a very strong promoter and this accounts for its widespread use for high level expression of traits in transgenic plants. The CaMV35S promoter however has also demonstrated relatively low activity in several agriculturally significant graminaceous plants such as wheat.

The promoters of the maize genes encoding alcohol dehydrogenase, AdhI and AdhII, have also been widely used in plant cell transformations. Both genes are induced after the onset of anaerobiosis. Maize AdhI has been cloned and sequenced as has been AdhII. Formation of an AdhI chimeric gene, Adh-CAT comprising the AdhI promoter linked to the chloramphenicol acetyltransferase (CAT) coding sequences and nopaline synthase (NOS) 3' signal caused CAT expression at approximately 4-fold higher levels at low oxygen concentrations than under control conditions. Sequence elements necessary for anaerobic induction of the ADH-CAT chimeric have also been identified. The existence of anaerobic regulatory element (ARE) between positions −140 and −99 of the maize AdhI promoter composed of at least two sequence elements at positions −133 to −124 and positions −113 to −99 both of which have found to be necessary and are sufficient for low oxygen expression of ADH-CAT gene activity. The Adh promoter however responds to anaerobiosis and is not a constitutive promoter, drastically limiting its effectiveness.

Yet another important promoter in plants is the maize ubiquitin promoter which is described in U.S. Pat. No. 5,510,474, to Quail et al. the disclosure of which is incorporated herein by reference. This promoter has become widely used in transgenic plant protocols. The promoter, as described in the patent, comprises RNA polymerase recognition and binding sites, a transcriptional initiation sequence (cap site), regulatory sequences responsible for inducible-transcription, an untranslatable intervening sequence (intron) between the transcriptional start site and the translational initiation site, and two overlapping heat shock consensus promoter sequences 5' (−214 and −204) of the transcriptional start site. The entire promoter is almost 2 kb in length and has been shown to be functional in both monocot and dicot plants. The sequence of the maize ubiquitin promoter is disclosed in Quail et al. Expression levels achieved with the ubiquitin (Ubi-1) promoter driving the CAT gene in oat protoplast cells were higher than those of the CaMV promoter (Quail et al.).

There is a continuing need in the art for high level expression promoters, as well as promoters which are spatially defined in their expression patterns.

Expression of foreign nucleotide sequences introduced to cells must achieve more than a basal expression rate to produce enough protein to effect the desired phenotype or to harvest from the cell.

It is a primary object of this invention to provide novel maize Ubi-1 promoter sequences that increase expression of introduced genes in plant cells and plant tissues, compared to the non-engineered promoter.

It is yet another object of the invention to provide promoter sequences which result in expression in transgenic plants which unexpectedly alters or reverses the ratio of endosperm/embryo expression from known Ubi-1 promoters in the seed of regenerated plants.

It is an object of this invention to provide recombinant promoter molecules that provide for reliably high levels of expression of introduced genes in target cells.

It is yet another object of this invention to provide plants, plant cells and plant tissues containing the recombinant promoter of the invention.

It is yet another object of the invention to provide vehicles for transformation of plant cells including viral or plasmid vectors and expression cassettes incorporating the novel promoter sequences of the invention.

It is yet another object of the invention to provide bacterial cells comprising such vectors for maintenance, replication, and plant transformation.

Other objects of the invention will become apparent from the description of the invention which follows.

SUMMARY OF THE INVENTION

The present invention comprises the design of novel regulatory nucleotide sequences which provide for improved expression of a nucleotide sequence, such as a structural gene, in plants, both monocotyledonous and dicotyledonous. According to the invention, several engineered versions of a maize ubiquitin promoter are described which provide for expression levels that are higher than that achieved with native ubiquitin promoters and which spatially provide for altered expression levels in the embryo and endosperm of seed of regenerated plants.

The invention further comprises expression cassettes comprising the promoters of the invention, a structural gene, the expression of which is desired in plant cells, and a polyadenylation or stop signal. The expression cassette can be encompassed in a plasmid or viral vector for transformation of plant cells.

The invention also encompasses transformed bacterial cells for maintenance and replication of the vector, as well as transformed monocot or dicot cells and ultimately transgenic plants, and breeding materials developed from the transgenic plants.

According to the invention, ubiquitin promoters are provided which differ from prior ubiquitin promoters primarily in the area of the heat shock region which comprises overlapping heat shock elements, to remove one of the elements, to remove the overlap of the sequences, or to delete both elements entirely. In a preferred embodiment binding domains for transcription factors may be inserted in this area. The interaction between the overlapping heat shock elements and the intron region with the rest of the 5' sequence in the ubiquitin promoter is unknown and was previously thought to be critical for full promoter function. See Quail, supra. Applicants have found that the promoter not only still functions adequately, despite prior teachings to the contrary but quite surprisingly have discovered that engineering in this region increases expression over the previous ubiquitin promoter system and alters the expression ratio of the protein from embryo to endosperm. The Ubi-1 promoter, previously thought to be constitutive has recently been shown to express preferentially in the seed, WO 98/139461 published Sep. 11, 1998, making the engineered promoters of the invention with endosperm expression surprising.

For purposes of this application the following terms shall have the definitions recited herein. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively engineered variants" applies to both amino acid and nucleic acid sequences. With respect to particular nucleic acid sequences, conservatively engineered variants refers to those nucleic acids which encode identical or conservatively engineered variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively engineered variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be engineered to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively engineered variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively engineered variants typically provide similar biological activity as the unengineered polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be engineered to account for the specific codon preferences and GC content preferences of monocotyledons or dicotyledons as these preferences have been shown to differ (Murray et al. *Nucl. Acids Res.* 17:477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN <u>AUGG</u>, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially engineered from its native form in composition and/or genomic locus by deliberate human intervention. For example, a promoter operably linked to a heterologous structural gene is from a species different from that from which the structural gene was derived, or, if from the same species, one or both are substantially engineered from their original form. A heterologous protein may originate from a foreign species or, if from the same species, is substantially engineered from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" or "nucleotide" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, $2^{nd}$ ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include engineered cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley, and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones engineered for stability or for other reasons as "polynucleotides" as that term is intended herein. Moreover, DNAs or RNAs comprising unusual bases, such as inosine, or engineered bases, such as tritylated bases, to name just two examples, are polynucleotides as the term is used herein. It will be appreciated that a great variety of engineering has been made to DNA and RNA that serve many useful purposes known to those of skill in the art. The term polynucleotide as it is employed herein embraces such chemically, enzymatically or metabolically engineered forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of engineering including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions, and in most plant parts.

As used herein "recombinant" includes reference to a cell or vector, that has been engineered by the introduction of a heterologous nucleic acid or that the cell is derived from a cell so engineered. Thus, for example, recombinant cells express genes that are not found in identical form within the native (non-recombinant) form of the cell or express native genes that are otherwise abnormally expressed, underexpressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and may be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≦90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, N.Y. (1995).

As used herein, the term "structural gene" includes any nucleotide sequence the expression of which is desired in a plant cell. A structural gene can include an entire sequence encoding a protein, an open reading frame or any portion thereof or also antisense. Examples of structural genes are included hereinafter are intended for illustration and not limitation.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often bacterial plasmids or replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237–244 (1988); Higgins and Sharp, CABIOS 5:151–153 (1989); Corpet, et al., *Nucleic Acids Research* 16:10881–90 (1988); Huang, et al., *Computer Applications in the Biosciences* 8:155–65 (1992), and Pearson, et al., *Methods in Molecular Biology* 24:307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul eta., *Nucleic Acids Res.* 25:3389–3402 (1997). Software for performing BLAST analyses is publicly available, e.g., through the National Center for Biotechnology-Information (world wide web at hcbi.nlm.nih.gov/). This algorithm involves first identifying high scoring sequence pairs (HSPs) by identiying short words of length W in the query sequence, which either match or satisfy some positive-valued threshold score T when aligned with a word of the same length in a database sequence. T is referred to as the neighborhood word score threshold (Altachul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X detennine the sensitivity and speed of the alignment. The BLASTN program (for nucleotide sequences) uses as defaults a wordlength (W) of 11, an expectation (E) of 10, a cutoff of 100, M=5, N=4, and a comparison of both sirands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e)(I) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial Identity" in the context of a peptide indicates that a peptide comprises a sequence with at least 70% sequence identity to a reference sequence, preferably 80%, or preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48:443 (1970). an indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

As used herein, the term "maize ubiquitin promoter", or "ubiquitin promoter", or "ubiquitin-1 promoter" or "Ubi-1 promoter" shall include a 5' promoter region from a gene encoding ubiquitin, or protein with the functional characteristics of ubiquitin, and shall include the 5' region of the maize ubiquitin gene described in Quail, bases −899–1092 including sequences which are capable of hybridizing under conditions of high stringency thereto.

As used herein the term "engineered ubiquitin promoter" or "Ubi-1 promoter variant" shall include a ubiquitin promoter which has a heat shock region that is engineered from its native state and which is capable of directing expression in a plant cell.

As used herein the term "heat shock region" shall include an area of a ubiquitin promoter sequence which comprises two overlapping heat shock elements and includes bases −214 to −189 of the sequence disclosed in Quail.

DESCRIPTION OF THE FIGURES

In FIG. 1A, embryogenic callus tissue is depicted. A mean level of GUS was determined among transformation events for each Ubi-1 variant. (GSB=wild type, yellow; GSC=HSEs deleted, GSD=3' HSE deleted, GSE=5' HSE deleted, GSF HSE adjacent, GSG =HSEs replaced by Ps1 trimer.

In FIG. 1B, leaf tissue of seedlings regenerated from tissue culture are depicted. A mean level of GUS was determined among one to eight plants derived from independent transformation events. From these data, a mean level of GUS was determined for each Ubi-1 variant. No data were available for GSD.

In FIG. 1C, T1 seed is depicted. The highest level of GUS was determined among five seeds for each T0 plant. A mean level of GUS was then determined for this high expressing seed among one to ten T0 plants for each independent transformation event. From these data, a mean level of GUS was determined for each Ubi-1 promoter variant. For FIGS. 1A, B and C, tissue with no GUS activity was not included in the analysis. The number of transformation events (n) per DNA construct is shown. 95% confidence levels are shown for the mean values. Note the difference in the y-axis scale for A, B and C.

Plants that produced no seed with GUS activity were not included in the analysis. The number of transformation events (n) per DNA construct is shown. 95% confidence levels are shown for the mean values.

Figure 3A:
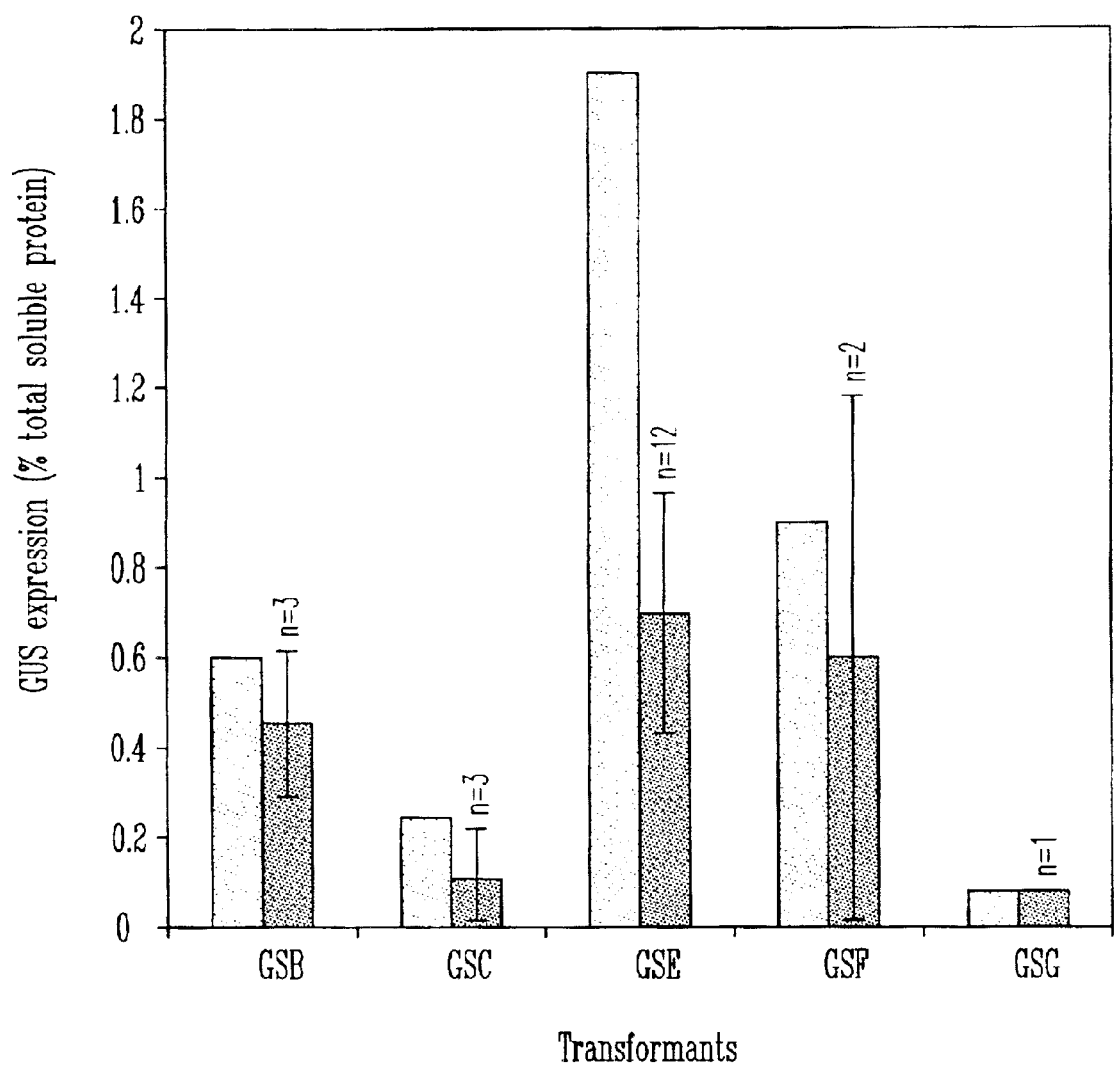
Figure 3B:
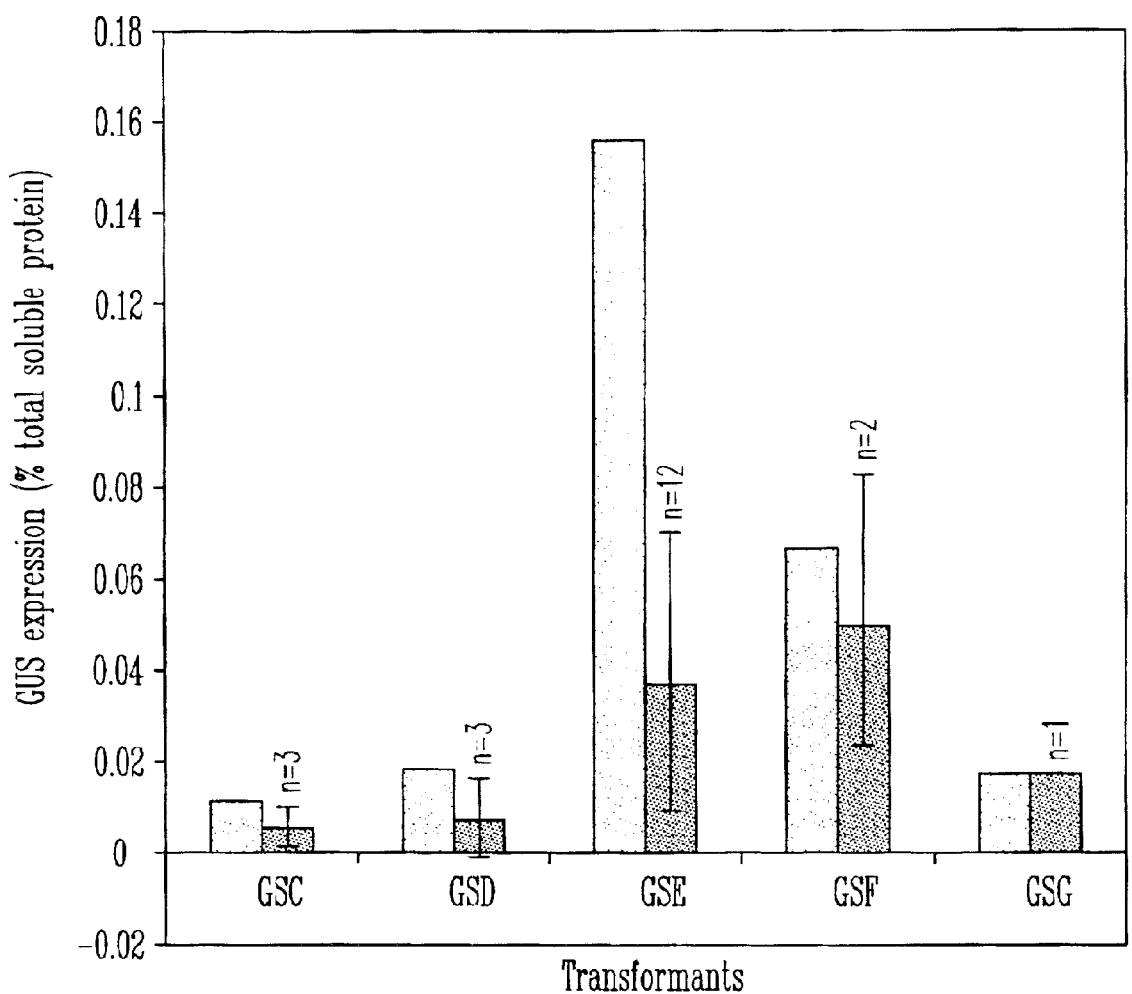

FIGS. 3A and 3B are graphs depicting expression of GUS in T1 seed and in leaves of T1 plants.

In FIG. 3A, the highest level of GUS was determined among five seeds for each T0 plant, and then these data were used to select the highest expressing seed pools derived from several of the independent transformation events. A highest recorded (light bar) and a mean (dark bar) level of GUS were then determined among the selected seed pools for each promoter variant.

In FIG. 3B, leaves were analyzed from three herbicide resistant T1 plants derived from each selected T1 seed pool, and the highest observed level of GUS in leaf tissue was recorded for each pool. From these data, a highest recorded (light bar) and a mean (dark bar) level of GUS were determined among the selected leaf tissue for each promoter variant. For FIGS. 3A and B, the number transformation events chosen (n) per DNA construct is shown. 95% confidence levels are shown for the mean values. Note the difference in the y-axis scale for A and B.

DETAILED DESCRIPTION OF THE INVENTION

The maize ubiquitin promoter has often been used to drive relatively high level expression of foreign genes in monocots, particularly economically important grasses (Cornejo, M. J., et al. (1993), "Activity of a maize ubiquitin promoter in transgenic rice", *Plant Mol. Biol.* 23:567–581) Examples of genes expressed from this promoter include bar/pat for herbicide selection, uidA for GUS reporter gene expression to score transformation and recently for xenogenic protein production in maize (Hood, E. E., et al. (1997), "Commercial production of avidin from transgenic maize: characterization of transformant, production, processing, extraction and purification", *Mol. Breed.* 3:291–306; Witcher, D. R., et al. (1998), "Commercial production of β-glucuronidase (GUS): a model system for the production of proteins in plants", *Mol. Breed* 4:301–312; Zhong, G-Y, et al. (1999), "Commercial production of aprotinin in transgenic maize seeds", *Mol. Breed,* 5:345–356).

Maize Ubi-1 is one of the highest expressed constitutive genes characterized in plants (Christensen et al., 1992, "Maize polyubiquitin genes: structure, thermal perturbation of expression and transcript splicing, and promoter activity following transfer to protoplasts by electroporation", *Plant Mol. Biol.* 18:675–689). Approximately 0.9 kb of 5' flanking sequence of Ubi-1, together with the 5' untranslated leader sequence and the first intron, are sufficient to drive expression of reporter genes in several monocot species (Christensen et al., 1992, supra; "Non-systemic expression of a stress-responsive maize polyubiquitin gene (Ubi-1) in transgenic rice plants", 1994, Takimoto et al., *Plant Mol. Biol.* 26:1007–1012; Christensen and Quail, 1996, "Ubiquitin promoter-based vectors for high-level expression of selectable and/or screenable marker genes in monocotyledonous plants", *Transgenic Res.* 5:213–218). The 5' flanking sequence of Ubi-1 includes regions with similarity to defined cis-acting elements. A TATA box is located in the consensus position, and two overlapping heat shock elements (HSEs) with similarity to the HSEs of *Drosophila melanogaster* genes (Pelham, H. R., et al. (1982), "A synthetic heat-shock promoter element confers heat-inducibility on the herpes simplex virus thymidine kinase gene", *EMBO J.,* 1:1473–1477) are located approximately 0.2 kb upstream of the transcription start site.

In an effort to develop constitutive promoters which effect even higher levels of foreign gene expression in callus, leaves or seeds of grass species, the Applicants have developed promoters which have different controlling elements than the native maize polyubiquitin-1 promoters. Engineering was focused on the overlapping heat shock elements (HSEs) ~200 bases 5' to the start of transcription. These elements were removed entirely, singly removed or placed in tandem as opposed to their native overlapping arrangement. A final variant contained a seed preferred binding domain in place of the native elements. Three of the five promoter variants effected higher level expression of GUS reporter protein in seed, and two of these were more effective in leaves than the wild type maize ubiquitin promoter. The new promoters are surprising as it was previously thought that two heat shock elements need be present and further that these elements were overlapping for functional promoter activity.

Quite surprisingly these novel promoters changed the tissue preference for expression, from primarily embryo expression to increased expression in the endosperm with decreased embryo expression. One of the variants completely reversed the ratio of embryo to endosperm expression resulting in an endosperm preferred expression profile.

According to the invention novel promoters have been designed which include ubiquitin promoter variants with engineering primarily of the heat shock region at –214–190 of the ubiquitin promoter.

Typically this region is comprised of two overlapping heat shock elements having the following sequence:

CTGGACCCC TCTCGA GAGTTCCGCT                (SEQ ID NO:1)

The 5' heat shock consensus sequence is underlined. The 3' heat shock consensus sequence is overlined. As can be seen, the overlap is a CTCGA 5-mer. According to the invention, novel promoters are designed which do not include two overlapping heat shock elements. Variants included, deletion of both heat shock elements, deletion of the 3' element, deletion of the 5' element, and removal of the overlap so that the two elements are adjacent.

A chart depicting the engineering in the heat shock region is below:

TABLE 1

Engineering of Ubi-1 promoter HSE

| DNA construct | DNA sequence[1] | HSE engineering | Transgenic lines |
|---|---|---|---|
| PGN7062 | CTGGACCCCTCTCGAGAGTTCCGCT (SEQ ID NO:1) | wild type | GSB |
| PGN7547 | ------------------------ | HSEs deleted | GSC |
| PGN7565 | CTGGACCCCTCTCGA---------- (SEQ ID NO:2) | 3'HSE deleted | GSD |
| PGN7583 | ----------CTCGAGAGTTCCGCT (SEQ ID NO:3) | 5'HSE deleted | GSE |
| PGN7600 | CTGGACCCCTCTCGACTCGAGAGTTC CGCT (SEQ ID NO:4) | HSEs adjacent | GSF |

TABLE 1-continued

Engineering of Ubi-1 promoter HSE

| DNA construct | DNA sequence[1] | HSE engineering | Transgenic lines |
|---|---|---|---|
| PGN8926 | 3x(GACACGTAGAATGAGTCATCAC) (SEQ ID NO:5) | HSEs replaced by Ps1 trimer | GSG |

[1]The 5' HSE is in bold type and the 3' HSE is underlined.

In yet another embodiment a transcription binding factor can be added in the engineered heat shock element region, to add in transcription of the sequences following the promoter. Such factors are known to those of skill in the art and include but are not limited to: the prolactin seed specific binding factor: (dePater, S., et al. (1994), "A 22-bp fragment of the pea lectin promoter containing essential TGAC-like motifs confers seed-specific gene expression", *Plant Cell* 5:877–886dePater, S., et al. (1996), "The 22 bp W1 element in the pea lectin promoter is necessary and, as a multimer, sufficient for high gene expression in tobacco seeds", *Plant Mol. Biol.* 32:515–523), and the basic domain/leucine zipper proteins TGA1a and Opaque-2 can bind this sequence in vitro (dePater, S., et al. (1994), "bZIP proteins bind to a palindromic sequence without and ACGT core located in a seed-specific element of the pea lectin promoter", *Plant J.* 6:133–140). A table of transcription factors which may be used according to the invention follows:

introduction of the recombinant DNA molecule, the plant species to be engineered, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural gene selection are other parameters which may be optimized to achieve desired plant expression or inhibition as is known to those of skill in the art and taught herein.

The following is a non-limiting general overview of Molecular biology techniques which may be used in performing the methods of the invention.

Structural Gene

Likewise, by means of the present invention, heterologous nucleotide sequences can be expressed in transformed plants. More particularly, plants can be genetically engineered to express various phenotypes of agronomic interest.

Exemplary genes include but are not limited to: plant disease resistance genes, (Martin et al., Science 262: 1432 (1993) (tomato Pto gene for resistance to *Pseudomonas syringae* pv. tomato encodes a protein kinase)); a *Bacillus thuringiensis* protein, (Geiser et al., Gene 48: 109 (1986); a lectin, (Van Damme et al., *Plant Molec. Biol.* 24: 25 (1994)); a vitamin-binding protein, (such as avidin. see PCT appli-

TABLE A

| Species | Factor | Target Gene | 5' extent of site | 3' extent of site | Site Sequence |
|---|---|---|---|---|---|
| Arabidopsis thaliana | EBP | Pathogenesis-related protein 1b | −207 | −192 | atGGCTctta (SEQ ID NO:6) |
| Arabidopsis thaliana | HY5 | Ribulose-1, 5-biphosphate carboxylase | −241 | −230 | CTTCCACGTGGCA (SEQ ID NO:7) |
| Hordeum vulgare | BLZ-1 | B-hordein | −252 | −220 | acatgtaaagtgaataagGTGAGTCA (SEQ ID NO:8) |
| Hordeum vulgare | Gamyb | High-pI alpha-amylas | −149 | −128 | ggccgaTAACAAACtccggccg (SEQ ID NO:9) |
| an Oryza sativa virus | RF2a | Rice tungro bacilliform virus promoter | −53 | −39 | CCAGTGTGCCCCTGG (SEQ ID NO:10) |
| Phaseolus vulgare | ROM1 | Phytohemagglutinin | −207 | −199 | GCCACGTCA |
| Pisum sativum | GT-1 | Ribulose-1, 5-biphosphate carboxylase | −257 | −245 | GATTTACACT (SEQ ID NO:11) |
| Triticum aestivum | SPA | Low molecular weight glutenin-1D1 | −256 | −241 | taaGGTGAGTCATata (SEQ ID NO:12) |
| Zea mays | Dof2 | C4-type phosphoenolpyruvate carboxylase | −774 | −765 | ATACTTTTC (SEQ ID NO:13) |
| Zea mays | Opaque-2 | 22-kD Zein | −305 | −288 | tgTCATTCCACGTAGAtg (SEQ ID NO:14) |

Transgenic Techniques Overview

Likewise, by means of the present invention, agronomic genes in combination with the promoters of the invention can be expressed in transformed plants. Production of a genetically engineered plant tissue either expressing or inhibiting expression of a structural gene combines the teachings of the present disclosure with a variety of techniques and expedients known in the art. In most instances, alternate expedients exist for each stage of the overall process. The choice of expedients depends on the variables such as the plasmid vector system chosen for the cloning and cation US93/06487); an enzyme inhibitor, (Abe et al., *J. Biol. Chem.* 262: 16793 (1987)); an insect-specific hormone or pheromone, (see, for example, Hammock et al., Nature 344: 458 (1990)); an insect-specific peptide or neuropeptide, (Regan, *J. Biol. Chem.* 269: 9 (1994)); an insect-specific venom, (Pang et al., *Gene* 116: 165 (1992); an enzyme responsible for an hyperaccumulation of a monterpene; an enzyme involved in the engineering, including the post-translational engineering, of a biologically active molecule; for example, a glycolytic enzyme, a proteolytic enzyme; (See PCT application WO 93/02197); a molecule that stimulates signal transduction, (for example, Botella et al., *Plant Molec. Biol.* 24: 757 (1994)); a hydrophobic moment peptide, (PCT application WO 95/16776); a membrane permease, (Jaynes et al., *Plant Sci.* 89: 43 (1993)); a viral-invasive protein or a complex toxin derived therefrom, (Beachy et al., *Ann. Rev. Phytopathol.*28: 451 (1990)); (Taylor et al., Abstract #497, SEVENTH IN'L SYMPOSIUM ON MOLECULAR PLANT-MICROBE INTERACTIONS (Edinburgh, Scotland, 1994)); a virus-specific antibody, (Tavladoraki et al., *Nature* 366: 469 (1993)); a developmental-arrestive protein produced in nature by a pathogen or a parasite, (Lamb et al., *Bio/Technology* 10: 1436 (1992)); a developmental-arrestive protein produced in nature by a plant, (Logemann et al., *Bio/Technology* 10: 305 (1992)); a herbicide that inhibits the growing point or meristem, such as an imidazalinone or a sulfonylurea, (Lee et al.,*EMBO J.* 7: 1241 (1988)); Glyphosate (resistance imparted by mutant 5-enolpyruvl-3-phosphikimate synthase (EPSP) and aroA genes, respectively) (U.S. Pat. No. 4,940, 835); a herbicide that inhibits photosynthesis, such as a triazine (psbA and gs+ genes) and a benzonitrile (nitrilase gene). (Przibilla et al., *Plant Cell* 3: 169 (1991)); Engineered fatty acid metabolism, for example, by transforming a plant with an antisense gene of stearoyl-ACP desaturase to increase stearic acid content of the plant. See Knultzon et al., *Proc. Natl. Acad. Sci. USA* 89: 2624 (1992); decreased phytate content, (Van Hartingsveldt et al., *Gene* 127: 87 (1993)); engineered carbohydrate composition, for example, by transforming plants with a gene coding for an enzyme that alters the branching pattern of starch. (See Shiroza et al., *J. Bacteriol.* 170: 810 (1988)); genes that controls cell proliferation and growth of the embryo and/or endosperm such as cell cycle regulators (Bogre L et al., "Regulation of cell division and the cytoskeleton by mitogen-activated protein kinases in higher plants." Results Probl Cell Differ 27:95–117 (2000).

Promoters

The promoters disclosed herein may be used in conjunction with naturally occurring flanking coding or transcribed sequences of the desired heterologous nucleotide sequence or structural gene or with any other coding or transcribed sequence that is critical to structural gene formation and/or function.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to seed specific Structural formation and/or function.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements.

Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different gene. Polyadenylation sequences include, but are not limited to the *Agrobacterium* octopine synthase signal (Gielen et al., *EMBO J.* (1984) 3:835–846) or the nopaline synthase signal (Depicker et al., *Mol. and Appl. Genet.* (1982) 1:561–573), or pin II the proteinase inhibitor II gene from potato.

Marker Genes

Recombinant DNA molecules containing any of the DNA sequences and promoters described herein may additionally contain selection marker genes which encode a selection gene product which confer on a plant cell resistance to a chemical agent or physiological stress, or confer a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis of RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance gene and the hygromycin resistance gene. Transformed plant cells thus selected can be induced to differentiate into plant structures which will eventually yield whole plants. It is to be understood that a selection marker gene may also be native to a plant.

Transformation

In accordance with the present invention, a transgenic plant is produced that contains a DNA molecule, comprised of elements as described above, integrated into its genome so that the plant expresses a heterologous gene-encoding DNA sequence. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al, "Procedures for Introducing Foreign DNA into Plants" in *Methods in Plant Molecular Biology and Biotechnology*, Glick et al (eds) pp. 67–68 (CRC Press 1993) and by Phillips et al, "Cell/Tissue Culture and In Vitro Manipulation" in *Corn and Corn Improvement* 3d Edit. Sprague et al (eds) pp. 345–387 (American Soc. Of Agronomy 1988). The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al, supra; Klein et al, *Bio/Technology* 10:268 (1992); and Weisinger et al., *Ann. Rev. Genet.* 22: 421–477 (1988). For example, the DNA construct may be introduced into the genomic DNA of the plant cell using techniques such as microprojectile-mediated delivery, Klein et al., *Nature* 327: 70–73 (1987); electroporation, Fromm et al., *Proc. Natl. Acad. Sci.* 82: 5824 (1985); polyethylene glycol (PEG) precipitation, Paszkowski et al., *Embo J.* 3: 2717–2722 (1984); direct gene transfer, WO 85/01856 and EP No. 0 275 069; in vitro protoplast transformation, U.S. Pat. No. 4,684,611; and microinjection of plant cell protoplasts or embryogenic callus. Crossway, *Mol. Gen. Genetics* 202:179–185 (1985). Co-cultivation of plant tissue with *Agrobacterium tumefaciens* is another option, where the DNA constructs are placed into a binary vector system. Ishida et al., "High Efficiency Transformation of Maize (*Zea mays* L.) Mediated by *Agrobacterium tumefaciens*" *Nature Biotechnology* 14:745–750 (1996). The virulence functions of the *Agrobacterium tumefaciens* host will direct the insertion of the construct into the plant cell DNA when the cell is infected by the bacteria. See, for example Horsch et al., *Science* 233: 496–498 (1984), and Fraley et al., *Proc. Natl. Acad. Sci.* 80: 4803 (1983).

Standard methods for transformation of canola are described by Moloney et al. "High Efficiency Transformation of *Brassica napus* Using *Agrobacterium Vectors*" *Plant Cell Reports* 8:238–242 (1989). Corn transformation is described by Fromm et al, *Bio/Technology* 8:833 (1990) and Gordon-Kamm et al, supra. *Agrobacterium* is primarily used in dicots, but certain monocots such as maize can be transformed by *Agrobacterium*. U.S. Pat. No. 5,550,318. Rice transformation is described by Hiei et al., "Efficient Transformation of Rice (*Oryza sativs* L.) Mediated by *Agrobacterium* and Sequence Analysis of the Boundaries of the T-DNA" *The Plant Journal* 6(2): 271–282 (1994), Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. Sorghum transformation is described by Casas et al, supra and by Wan et al, *Plant Physiology* 104:37 (1994). Soybean transformation is described in a number of publications, including U.S. Pat. No. 5,015,580.

In one preferred method, the *Agrobacterium* transformation methods of Ishida supra and also described in U.S. Pat. No. 5,591,616, are generally followed, with engineering that the inventors have found improve the number of transformants obtained. The Ishida method uses the A188 variety of maize that produces Type I callus in culture. In one preferred embodiment the High II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid.

Further, the Ishida protocol as described provides for growing fresh culture of the *Agrobacterium* on plates, scraping the bacteria from the plates, and resuspending in the co-culture medium as stated in the '616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5g sucrose and 36 g glucose, all at a pH of 5.8. In a further preferred method, the bacteria are grown overnight in a 1 ml culture, then a fresh 10 ml culture re-inoculated the next day when transformation is to occur. The bacteria grow into log phase, and are harvested at a density of no more than OD600=0.5 and is preferably between 0.2 and 0.5. The bacteria are then centrifuged to remove the media and resuspended in the co-culture medium. Since Hi II is used, medium preferred for Hi II is used. This medium is described in considerable detail by Armstrong, C. I. and Green C. E. "Establishment and maintenance of friable, embryogenic maize callus and involvement of L-proline" Planta (1985) 154:207–214. The resuspension medium is the same as that described above. All further Hi II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross plants containing both DNA sequences or recombinant DNA molecules.

Expression of recombinant DNA molecules containing the DNA sequences and promoters described herein in transformed plant cells may be monitored using Northern blot techniques and/or Southern blot techniques or PCR-based methods known to those of skill in the art.

A large number of plants have been shown capable of regeneration from transformed individual cells to obtain transgenic whole plants. Corn has long been a successful plant transformation recipient. Fromm, et al., Bio Technology, 8:33 (1990). Others are as follows. For example, regeneration has been shown for dicots as follows: apple, Malus pumila (James et al., *Plant Cell Reports* (1989) 7:658); blackberry, Rubus, Blackberry/raspberry hybrid, Rubus, red raspberry, Rubus (Graham et al., *Plant Cell, Tissue and Organ Culture* (1990) 20:35); carrot, *Daucus carota* (Thomas et al., *Plant Cell Reports* (1989) 8:354; Wurtele and Bulka, *Plant Science* (1989) 61:253); cauliflower, *Brassica oleracea* (Srivastava et al., *Plant Cell Reports* (1988) 7:504); celery, *Apium graveolens* (Catlin et al., *Plant Cell Reports* (1988) 7:100); cucumber, *Cucumis sativus* (Trulson et al., Theor. *Appl. Genet.* (1986) 73:11); eggplant, *Solanum melonoena* (Guri and Sink, *J. Plant Physiol.* (1988) 133:52) lettuce, *Lactuca sativa* (Michelmore et al., *Plant Cell Reports* (1987) 6:439); potato, *Solanum tuberosum* (Sheerman and Bevan, *Plant Cell Reports* (1988) 7:13); rape, *Brassica napus* (Radke et al., Theor. *Appl. Genet.* (1988) 75:685; Moloney et al., *Plant Cell Reports* (1989) 8:238); soybean (wild), *Glycine canescens* (Rech et al., *Plant Cell Reports* (1989) 8:33); strawberry, *Fragaria x ananassa* (Nehra et al., *Plant Cell Reports* (1990) 9:10; tomato, *Lycopersicon esculentum* (McCormick et al., *Plant Cell Reports* (1986) 5:81); walnut, *Juglans regia* (McGranahan et al., *Plant Cell Reports* (1990) 8:512); melon, *Cucumis melo* (Fang et al., 86th Annual Meeting of the American Society for Horticultural Science *Hort. Science* (1989) 24:89); grape, *Vitis vinifera* (Colby et al., Symposium on Plant Gene Transfer, UCLA Symposia on Molecular and Cellular Biology *J Cell Biochem Suppl* (1989) 13D:255; mango, *Mangifera indica* (Mathews, et al., symposium on Plant Gene Transfer, UCLA Symposia on Molecular and Cellular Biology *J Cell Biochem Suppl* (1989) 13D:264); and for the following monocots: rice, *Oryza sativa* (Shimamoto et al., *Nature* (1989) 338:274); rye, *Secale cereale* (de la Pena et al., *Nature* (1987) 325:274); maize, (Rhodes et al., *Science* (1988) 240:204).

In addition, regeneration of whole plants from cells (not necessarily transformed) has been observed in apricot, *Prunus armeniaca* (Pieterse, *Plant Cell Tissue and Organ Culture* (1989) 19:175); asparagus, *Asparagus officinalis* (Elmer et al., *J. Amer. Soc. Hort. Sci.* (1989) 114:1019); Banana, hybrid Musa (Escalant and Teisson, *Plant Cell Reports* (1989) 7:665); bean, *Phaseolus vulgaris* (McClean and Grafton, *Plant Science* (1989) 60:117); cherry, hybrid Prunus (Ochatt et al., *Plant Cell Reports* (1988) 7:393); grape, *Vitis vinifera* (Matsuta and Hirabayashi, *Plant Cell Reports,* (1989) 7:684; mango, *Mangifera indica* (DeWald et al., *J Amer Soc Hort Sci* (1989) 114:712); melon, *Cucumis melo* (Moreno et al., *Plant Sci letters* (1985) 34:195); ochra, *Abelmoschus esculentus* (Roy and Mangat, *Plant Science* (1989) 60:77; Dirks and van Buggenum, *Plant Cell Reports* (1989) 7:626); onion, hybrid Allium (Lu et al., *Plant Cell Reports* (1989) 7:696); orange, *Citrus sinensis* (Hidaka and Kajikura, Scientia Horiculturae (1988) 34:85); papaya, *Carrica papaya* (Litz and Conover, *Plant Sci Letters* (1982) 26:153); peach, *Prunus persica* and plum, *Prunus domestica* (Mante et al., *Plant Cell Tissue and Organ Culture* (989) 19:1); pear, *Pyrus communis* (Chevreau et al., *Plant Cell Reports* (1988) 7:688; Ochatt and Power, *Plant Cell Reports* (1989) 7:587); pineapple, *Ananas comosus* (DeWald et al., *Plant Cell Reports* (1988) 7:535); watermelon, *Citrullus vulgaris* (Srivastava et al., *Plant Cell Reports* (1989) 8:300); wheat, *Triticum aestivum* (Redway et al., *Plant Cell Reports* (1990) 8:714).

The regenerated plants are transferred to standard soil conditions and cultivated in a conventional manner. After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

According to a preferred embodiment, the transgenic plant provided for commercial production of foreign protein is maize. In another preferred embodiment, the biomass of interest is seed. For the relatively small number of transgenic plants that show higher levels of expression, a genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton,1993) . Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

As indicated above, it may be desirable to produce plant lines which are homozygous for a particular gene. In some species this is accomplished rather easily by the use of anther culture or isolated microspore culture. This is especially true for the oil seed crop *Brassica napus* (Keller and Armstrong, Z. flanzenzucht 80:100–108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by Southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a engineered protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The following examples serve to better illustrate the invention described herein and are not intended to limit the invention in any way. All references cited herein are hereby expressly incorporated to this document in their entirety by reference.

EXAMPLES

Methods

Construction of Ubi-1 Promoter Variants

The DNA construct PHP8904 (Pioneer Hi-Bred; Johnston, Iowa), contains the GUS reporter gene positioned 3' to approximately 0.9 kb of 5' flanking sequence of maize Ubi-1, plus the Ubi-1 5' untranslated leader sequence and first intron. The potato proteinase inhibitor II transcription terminator region is present 3' of GUS. PHP8904 also carries right and left border sequences of an *Agrobacterium tumefaciens* Ti plasmid, bacterial antibiotic resistance and origin of replication sequences, and the bar gene of *Streptomyces hygroscopicus*, conferring resistance to the herbicide bialaphos. The construct PGN7062 is essentially identical to 8904, except that the GUS reporter gene includes sequences encoding six C-terminal histidine residues. All subsequent constructs are similar to PGN7062 but have engineering in Ubi-1 5' flanking sequences (Table 1). For each Ubi-1 5' flanking sequence variant, a series of oligonucleotides were generated that together span the putative heat shock elements. These oligonucleotides were assembled and the sequences amplified by the polymerase chain reaction. The DNA fragments were introduced into the cloning vector pCR2.1 (Invitrogen; Carlsbad, Calif.). SalI-BglII restriction enzyme generated DNA fragments spanning the engineered HSEs were isolated from the pCR2.1 based plasmids and were transferred into an intermediate PGEM (Promega Corporation; Madison, Wis.) based plasmid, PGN5796, so replacing corresponding wild type Ubi-1 5' flanking sequence. HindIII-NheI restriction enzyme generated DNA fragments, spanning the entire Ubi-1 5' flanking sequence and 5' untranslated region plus part of the first intron, were then transferred into PGN7062, so replacing corresponding wild type Ubi-1 sequence.

TABLE 1

Engineered Ubi-1 promoter HSE

| DNA construct | DNA sequence[1] | description | Transgenic lines |
|---|---|---|---|
| PGN7062 | CTGGACCCCTCTCGAGAGTTCCGCT (SEQ ID NO:1) | wild type | GSB |
| PGN7547 | -------------------------- | HSEs deleted | GSC |
| PGN7565 | CTGGACCCCT<u>CTCGA</u>---------- (SEQ ID NO:2) | 3' HSE deleted | GSD |
| PCN7583 | ----------CTCGAGAGTTCCGCT (SEQ ID NO:3) | 5' HSE deleted | GSE |
| PGN7600 | CTGGACCCCTCTCGAT<u>CGAGAGTTCC GCT</u> (SEQ ID NO:4) | HSEs adjacent | GSF |
| PGN8926 | 3X(GACACGTAGAATGACTCATCAC) (SEQ ID NO:5) | HSEs replaced by Ps1 trimer | GSG |

[1]The 5' HSE is in bold type and the 3' HSE is underlined.

Transient Transformation

Transient transformations using *Agrobacterium tumefaciens* were performed using sonication-assisted *Agrobacterium* transformation as described by Trick and Finer (Trick, H. N. et al. (1997) SAAT: Sonication assisted *Agrobacterium*-mediated transformation", *Transgenic Res.* 6:329–336). Ten immature zygotic embryos per tube were sonicated in the presence of *Agrobacterium tumefaciens* EHA 101 (pSB111) at an $O.D._{600\ nm}$ of 0.5 for 30 s, were placed onto co-cultivation medium and were incubated for 5 days. Embryos were stained for 24 hours with 5 mgml$^{-1}$ X-gluC (5-bromo-4-chloro-3-indolyl-β-D-glucoronic acid: cyclohexyl ammonium salt) (Inalco; Milan, Italy) dissolved in Jefferson's buffer (Jefferson, R. A. (1987), "Assaying chimeric genes in plants: the GUS gene fusion system", *Plant Molec. Biol. Reporter* 5:387–405). They were subsequently transferred to 70% ethanol.

Transformation, Tissue Culture and Plant Growth

The procedure for stable transformation followed a engineered version of Ishida et al. (Ishida, Y. et al. (1996), "High efficiency transformation of maize (*Zea mays* L.) mediated by *Agrobacterium tumefaciens*", *Nature Biotech* 14:745–750) and Armstrong and Green (Armstrong, C. L., et al. (1985) "Establishment and maintenance of friable, embryogenic maize callus and the involvement of L-proline", *Planta* 164:207–214). Transformation and regeneration media are described in Table 2. Immature zygotic embryos were isolated from Hi-II maize kernels at 12 days after pollination and were transformed with *Agrobacterium tumefaciens* strain EHA 101 containing the engineered Ubi-1 variant constructs. For *Agrobacterium* infection, bacteria were grown overnight in YEP liquid medium supplemented with antibiotic. *Agrobacterium* were then re-inoculated into YEP supplemented with 100 mgl$^{-1}$ kanamycin and 100 mgl$^{-1}$ spectinomicin and were grown to an $OD_{550\ nm}$ of 0.4–0.6. The *Agrobacterium* culture was centrifuged to remove the media and the pellet was resuspended in inoculation medium. Immature zygotic embryos were washed with inoculation medium and immersed in the *Agrobacterium* solution, vortexed for 30 s, incubated for 5 minutes and plated and co-cultivated for 4 days on solid co-culture medium. Embryos were transferred for three days onto non-selective medium supplemented with 100 mg/l carbenicillin, and then subcultured to Bialaphos selection medium and subsequently subcultured every two weeks. Embryogenic tissue (events) proliferating on selection media were excised and cultured on the same medium for proliferation for four weeks and were then subcultured onto regeneration medium for three weeks to allow embryo formation. Embryos were picked and transferred to germination medium for one to two weeks with light at 28° C. Plants that regenerated were transferred to tubes for root and shoot elongation. Multiple T0 plants were regenerated from embryogenic tissues that were selected on Bialaphos and these were transferred to a greenhouse. T0 plants were crossed with elite inbred lines to produce T1 seeds. For analysis of T1 leaves, T1 seeds were germinated in a greenhouse and were leaf painted with a 1% active ingredient of Finale® for selection of transformed plants. Leaf samples were collected three weeks after germination.

Preparation of Plant Extracts

For seed extracts, individual dry seeds were pulverized using a hammer and extracted with 500 μl of lysis buffer (50 mM sodium phosphate pH 7.0, 1 mM EDTA, 10 mM β-mercaptoethanol). Samples were placed in extraction tubes, each with a ball bearing added, in a Beckman rack and were homogenized in a high speed shaker for 20 s. Samples were centrifuged, and the supernatants recovered and stored on ice prior to analysis. For leaf extracts, small portions of the ends of leaves were cut off and pulverized under liquid nitrogen. Weights were recorded and extractions completed using lysis buffer at 10 μl per mg of sample. For callus extracts, samples were extracted using lysis buffer at 1 μl per mg of callus tissue. Protein concentrations were determined according Bradford (1976).

β-glucuronidase Activity Assay

GUS assays were performed as described by Jefferson (1987, supra). Total soluble protein (1 μg) was incubated in 100 μl of lysis buffer and the reaction initiated with 25 μl of 5 mM 4-methylumbelliferyl β-D-glucuronide (MUG, Sigma M-9130). The reaction was incubated for up to 20 minutes at 37° C. At specific time points 25 μl volumes of the reaction mixture were transferred to a Dynatech Microfluor reading plate that had 175 μl of stop buffer (0.2M $Na_2CO_3$) per well. Fluorescence was measured at an excitation wavelength of 360 nm and an emission wavelength of 460 nm on a Microplate Fluorometer (Cambridge Technologies 7625). GUS protein levels were then calculated by comparison to a standard curve of 1 –100 μM 4-methylumbelliferyl (MU, Sigma M-1508).

Results

Conserved Ubi-1 Promoter Sequences are not Required for Transient Expression in Maize Embryos To investigate whether engineered versions of the maize Ubi-1 promoter would facilitate high levels of constitutive expression, we generated a series of fusions of native or engineered Ubi-1 sequences to the GUS reporter gene for introduction into plants. The putative HSEs of the Ubi-1 promoter were removed, their relative spacing was altered or they were substituted with a trimer of a seed specific element from the promoter of the pea lectin gene Ps1 (Table 1).

The promoter variants were first assessed in a transient transformation system. The DNA constructs were introduced into zygotic embryos of maize and GUS activity was detected qualitatively by histochemical staining.

TABLE 2

| Transient transformants | Mean GUS expression score (relative values) |
|---|---|
| GSB | 2.1 |
| GSC | 2.0 |
| GSD | 1.7 |
| GSE | 2.5 |
| GSF | 2.1 |
| GSG | 2.2 |
| promoterless GUS | 0.0 |
| no vector | 0.0 |

*Score system: 3 = high, 2 = medium; 1 = low; 0 = nothing

In all cases, GUS is synthesized, indicating that none of the engineering to the Ubi-1 promoter knock out expression. However, embryos transiently transformed with PGN8926 produce much less GUS than those transformed with the other constructs.

Engineering of Conserved Ubi-1 Promoter Sequences can Increase Expression in Stable Transformed Lines of Maize To more accurately assess the engineered Ubi-1 promoter variants, stable transformed lines were developed. The series of GUS fusions were introduced into zygotic embryos of maize to generate stable transformation events. Multiple seedlings were regenerated from embryogenic callus tissue of each event to give transformed lines, and seedlings matured and flowered to generate T1 seeds. GUS activity was determined in embryogenic callus tissue, leaves of seedlings regenerated from tissue culture and T1 seeds. The native Ubi-1 5' flanking sequence and the promoter variants of Ubi-1 all drive GUS expression in each tissue type, but levels of GUS are much lower in embryogenic callus and in leaf tissue than in seeds.

Among plants derived from any specific transformation event, considerable variation in the level of GUS expression exists in leaves of regenerated seedlings and in T1 seeds. In addition, GUS expression in embryogenic callus tissue, leaves of regenerated seedlings and T1 seeds varies between different transformation events.

Figure 1A:
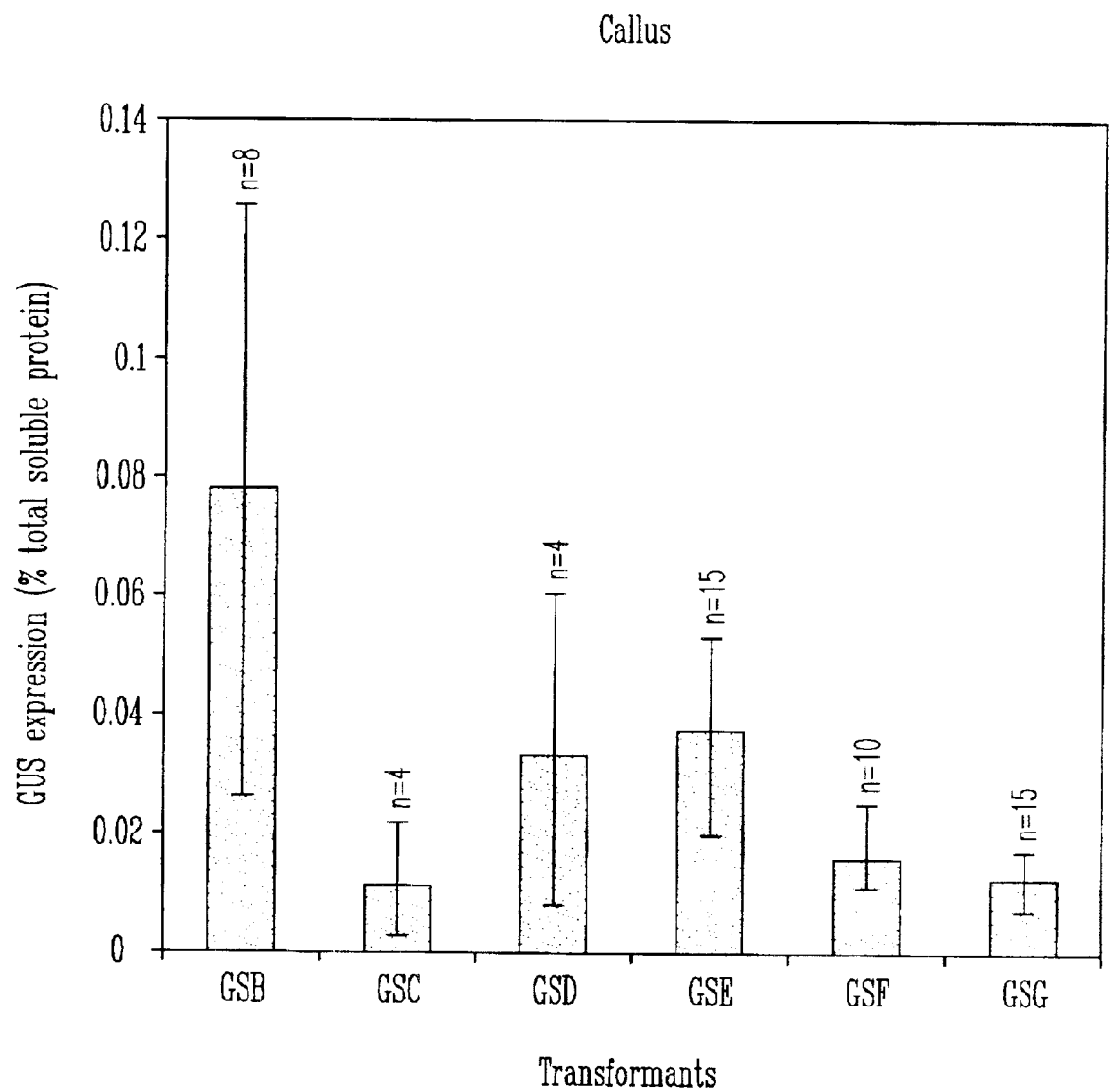
FIGS. 1A, 1B and 1C are graphs showing expression of GUS driven by Ubi-1 engineered promoter variants in tissues derived from independent stable transformation events.
Figure 1B:
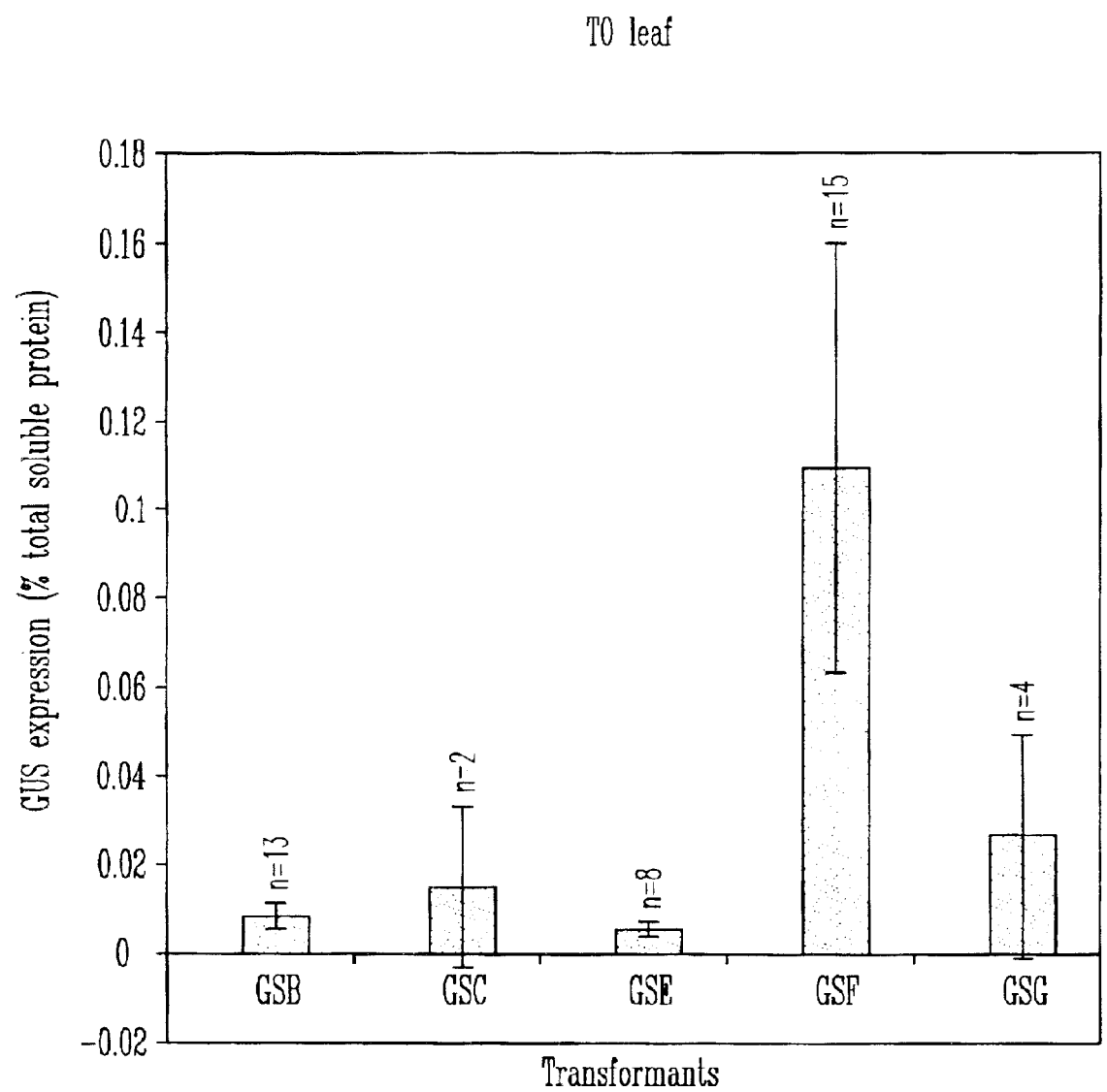
Figure 1C:
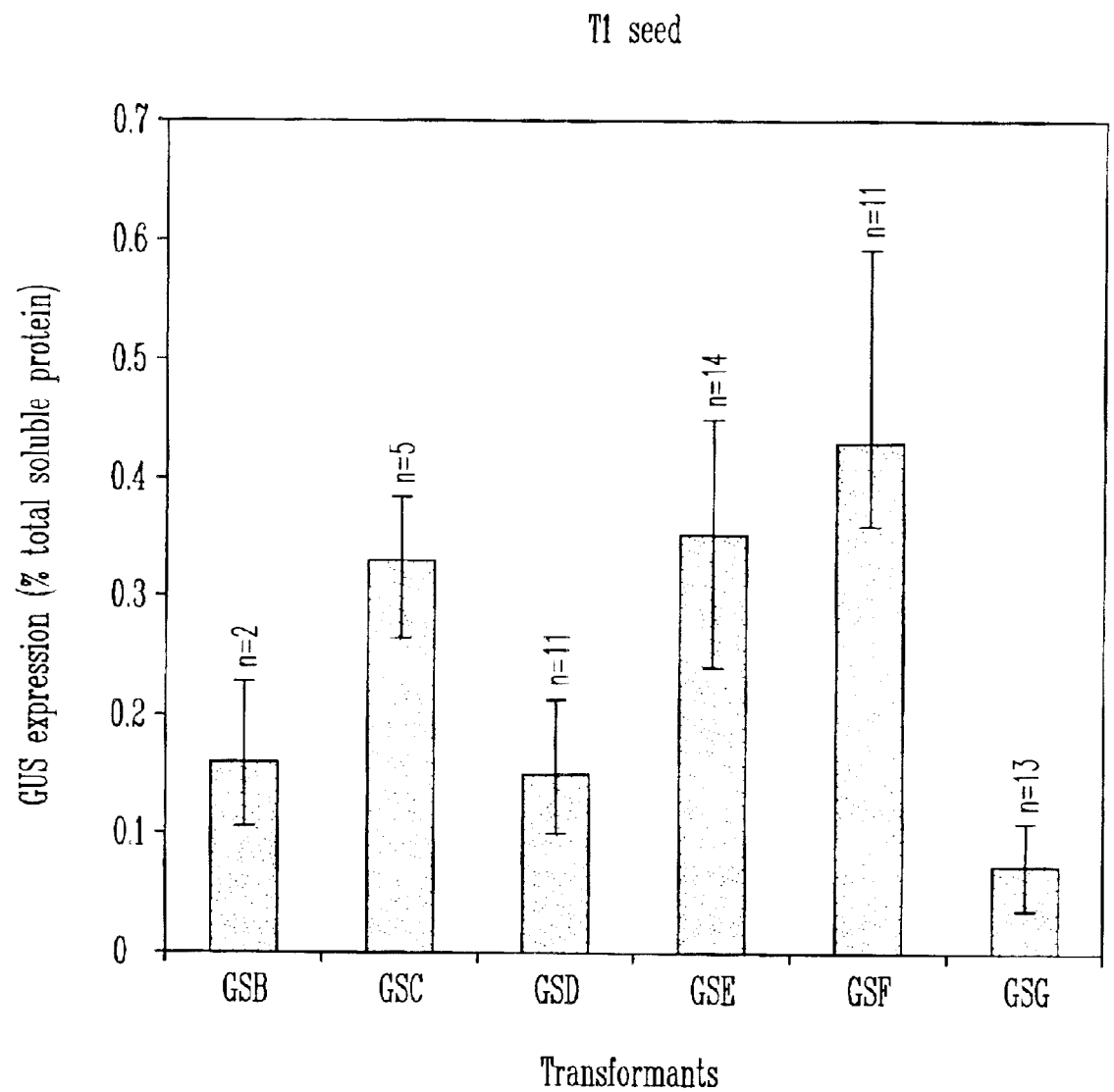
Figure 2:
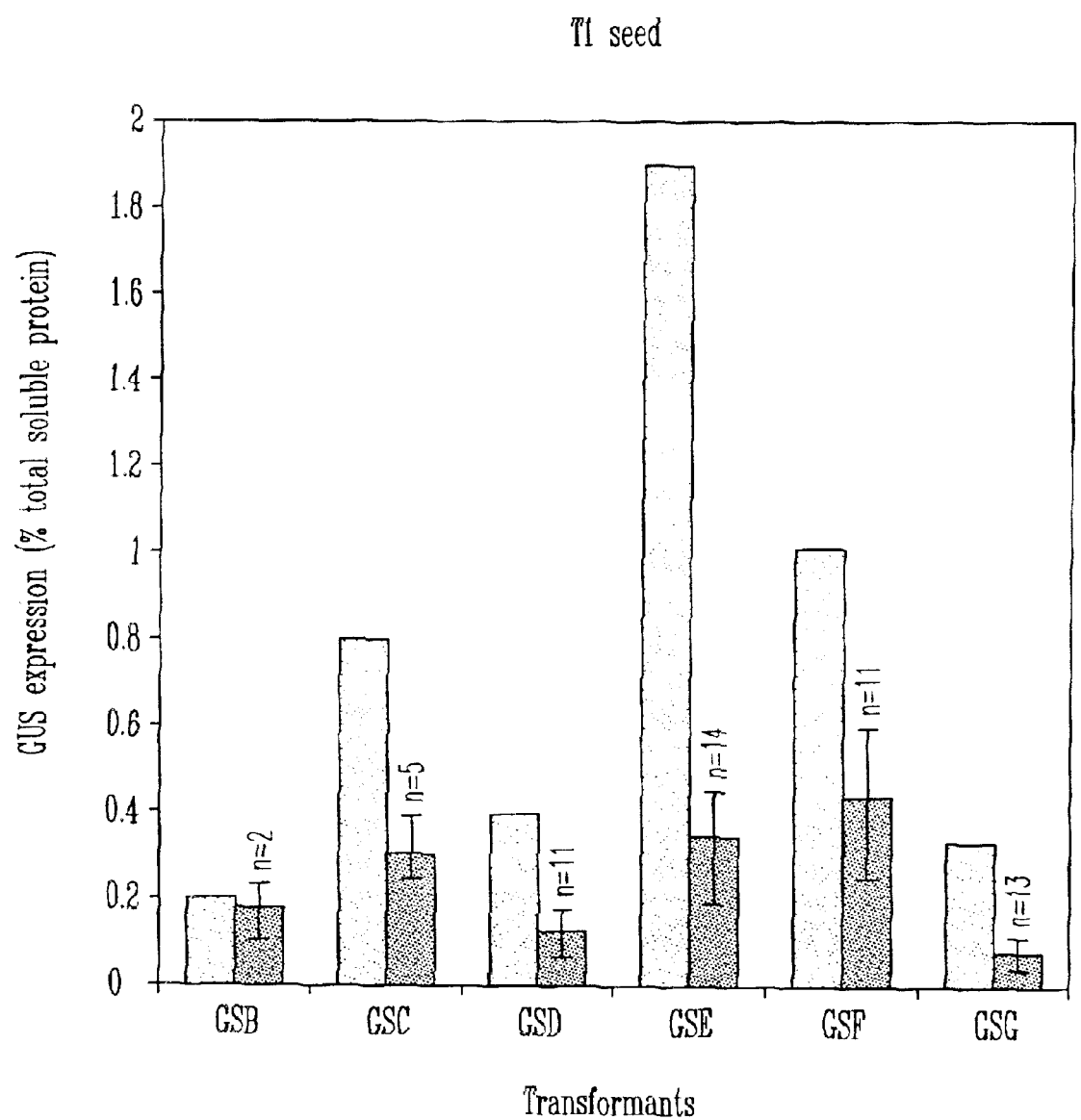
FIG. 2 is a graph depicting expression of GUS driven by Ubi-1 promoter variants in T1 seed of stable transformed lines. The highest level of GUS was determined among five seeds for each T0 plant. A mean level of GUS was then determined for this high expressing seed among one to ten T0 plants for each independent transformation event. From these data, a highest recorded (light bar) and a mean (dark bar) level of GUS were determined for each Ubi-1 variant.

However, focusing on T1 seed, which is the preferred site of expression for the commercial production of foreign proteins in corn, there are significant differences in mean levels of expression between transformed lines carrying the engineered promoters. GSD and GSG lines have levels of GUS expression similar to the control GSB line, but surprisingly, GSC, GSE and GSF lines have elevated expression levels (FIG. 1C). A ranking of GUS expression levels in T1 seed between lines transformed with the promoter variants is similar whether mean or highest recorded expression levels are considered (FIG. 2).

Ubi-1 Promoter Variants Drive Constitutive Expression but Have Tissue Preferences in the Kernel Maize Ubi-1 is constitutively expressed and the Ubi-1 promoter can drive the constitutive expression of reporter genes in transgenic plants (Christensen, A. H., et al. (1992), "Maize polyubiquitin genes: structure, thermal perturbation of expression and transcript splicing, and promoter activity following transfer to protoplasts by electroporation", *Plant Mol. Biol.* 18:675–689; Takimoto, I., et al. (1994), "Non-systemic expression of a stress-responsive maize polyubiquitin gene (Ubi-1) in transgenic rice plants", *Plant Mol. Biol.* 26:1007–1012; Christensen, A. H., et al. (1996), "Ubiquitin promoter-based vectors for high-level expression of selectable and/or screenable marker genes in monocotyledonous plants", *Transgenic Res.* 5:213–218). The engineered Ubi-1 promoter variants generated here drive expression of GUS in embryogenic callus tissue and leaves of seedlings regenerated from tissue culture. To examine whether the promoter variants cause constitutive expression in plants germinated from seed, a selection of transformed lines that express GUS at a high level in T1 seeds were analyzed. GUS activity was determined in leaf tissue of developing T1 seedlings and was compared to the activity that had been recorded for T1 seeds (FIG. 3). GUS was detected in leaves of transformed lines carrying all engineered Ubi-1 promoter variants, but expression was much lower than in seeds. Due to small selected sample sizes, there is considerable variation in the expression data among lines carrying each engineered promoter variant. However, the ranking of GUS expression in leaf tissue among the variants reflects the ranking in seed, except that in GSC lines expression ranks higher in seed than in leaf tissue.

The activity of the Ubi-1 promoter variants was also assessed visually in various tissues. Selected T1 kernels were either directly analyzed by cutting into sections and staining for GUS activity, or were germinated to generate seedlings of which root and leaf tissues were analyzed. GUS activity is observed in leaves and roots with all transformed lines, and in both tissue types is highest for GSE (5' HSE deleted) and GSF (HSE's adjacent) lines. In kernels of GSB lines GUS expression is higher in the embryo than in the endosperm. In transformed lines carrying the Ubi-1 promoter variants the distribution of GUS activity is more uniform across the seed, indicating increased expression in the endosperm compared to lines transformed with the native promoter sequence.

TABLE 3

Root and leaf qualitative data

| Construct | Mean root | Mean leaf |
|---|---|---|
| GSB | 2.0 | 2.0 |
| GSC | 2.3 | 2.7 |
| GSD | 3.0 | 2.8 |
| GSE | 3.7 | 3.6 |

TABLE 3-continued

Root and leaf qualitative data

| Construct | Mean root | Mean leaf |
|---|---|---|
| GSF | 4.0 | 3.7 |
| GSG | 3.0 | 2.0 |

*Score on a scale of 0 to 4 (−, +/−, +, ++, +++)

Tissue specific expression within the seed was further investigated by dissecting apart embryos and endosperm, and then determining expression levels separately. GSB (wild type) lines have a strong tissue type bins in the expression of GUS, with over 90% of the total activity in the embryo. GSD(3' HSE deleted), GSE (5' HSE deleted) and GSF lines show a lesser degree of embryo preferred expression, GSD (3' HSE deleted) lines have a similar level of GUS in each tissue and GSG (HSE's replaced by PsI trimer) lines have much more GUS in the endosperm. IN fact, with GSG (HSE's replaced by PsI trimer) lines the activity of the engineered Ubi-1 promoter is similar in the embryo and endosperm, but since the endosperm is about 7.5-fold larger than the embryo, most of the GUS is in the embryo.

TABLE 4

| Transformants | Seed fraction | Proportion of GUS |
|---|---|---|
| GSB | embryo | 0.92 |
| | endosperm | 0.08 |
| GSC | embryo | 0.89 |
| | endosperm | 0.11 |
| GSD | embryo | 0.47 |
| | endosperm | 0.53 |
| GSE | embryo | 0.83 |
| | endosperm | 0.17 |
| GSF | embryo | 0.21 |
| | endosperm | 0.79 |
| GSG | embryo | 0.15 |
| | endosperm | 0.85 |

As can be seen, the expression for GSC, GSD, GSE, GSF and GSG all had altered ratios of embryo/endosperm expression. GSD had almost 50/50 and GSG had the ratio reversed with endosperm expression preferred.

Discussion

Several maize Ubi-1 promoter sequences with engineering to the putative HSEs were used to drive GUS expression in transgenic corn seed. Surprisingly, deletion or engineering of the elements does not significantly reduce expression of a reporter gene. Rather, with some Ubi-1 promoter variants, expression of GUS is increased. Deletion of both putative HSEs or of the 5' element alone significantly increases expression, as does placing the elements adjacent so that they no longer overlap. Thus, engineering to the 5' putative HSE increase the level of expression in seed. In the case of re-positioning the elements to remove overlap, the affect may be to inadvertently diminish the activity of the 5' putative HSE by altering immediately adjacent sequence. Since removal or engineering of the 5' element appears to increase expression of a reporter gene in seed, the element may restrict expression under standard growth conditions in the context of the native Ubi-1 promoter. Surprisingly, replacement of the putative HSEs with a trimer of a 22 base pair sequence from the promoter of the pea lectin gene, Ps1, does not lead to increased expression. Although the Ps1 derived element does not include a HSE consensus sequence, it does include a five out of seven base pair match to the sequence GACCCCT within the 5' putative HSE of the Ubi-1 promoter, and this sequence may substitute for the 5' element.

The wild type Ubi-1 sequence analyzed here drives constitutive expression of GUS. Expression is observed in leaf and root tissue and is particularly high in seed tissue. Within the kernel expression is seen in both embryo and endosperm tissues, but is preferred in the embryo. This seed and specifically embryo-preferred expression is in agreement with previous work using Ubi-1 promoter sequences in stable transformed lines (Hood, E. E., et al. (1997), "Commercial production of avidin from transgenic maize: characterization of transformant, production, processing, extraction and purification", Mol. Breed. 3:291–306; Witcher et al., 1998, supra; Zhong et al., 1999, supra) and in embryos transiently transformed by microparticle bombardment Like the wild type sequence all of the Ubi-1 promoter variants examined here cause constitutive expression, with GUS being synthesized in leaf, root and especially seed tissue. However, within the kernel, there are notable differences in the balance of expression between embryo and endosperm tissue. None of the Ubi-1 promoter variants are as strongly embryo biased as the wild type sequence, indicating that within the kernel, the putative HSEs favor expression in embryo tissue.

Replacing the putative HSEs with a trimer of the Ps1 promoter element results in similar promoter activity in embryo and endosperm tissue, thus because of the relative tissue mass, a greater accumulation of transgene product in the endosperm. When fused to a minimal promoter, the Ps1 trimer confers seed-preferred expression in tobacco (dePater, S., et al. (1994), "A 22-bp fragment of the pea lectin promoter containing essential TGAC-like motifs confers seed-specific gene expression", Plant Cell 5:877–886dePater, S., et al. (1996), "The 22 bp W1 element in the pea lectin promoter is necessary and, as a multimer, sufficient for high gene expression in tobacco seeds", Plant Mol. Biol. 32:515–523), and the basic domain/leucine zipper proteins TGA1a and Opaque-2 can bind this sequence in vitro (dePater, S., et al. (1994), "bZIP proteins bind to a palindromic sequence without and ACGT core located in a seed-specific element of the pea lectin promoter", Plant J. 6:133–140). Opaque-2 is a well characterized transcription factor of maize endosperm, and may be binding to the Ps1 trimer introduced into the Ubi-1 promoter, so facilitating expression in the endosperm. Since the overall level of transgene expression in the seed is similar in lines transformed with native Ubi-1 sequences, or with a promoter in which a Ps1 trimer replaces the HSEs, the Ps1 trimer must act to reduce expression in the embryo, as well as to increase expression in the endosperm.

What is claimed is:

1. An engineered ubiquitin promoter sequence capable of directing expression of a nucleotide sequence in a plant cell, said engineered ubiquitin promoter sequence comprising: a heat shock region, wherein said heat shock region has the sequence as set forth in SEQ ID NO: 4.

2. A method for causing expression of a heterologous structural gene or open reading frame in a plant cell, said method comprising:

introducing to a plant cell an expression construct comprising an engineered ubiquitin promoter sequence operably linked to said heterologous structural gene or open reading frame, wherein said engineered ubiquitin promoter sequence comprises a heat shock region, wherein said heat shock region has the sequence as set forth in SEQ ID NO: 4.

* * * * *